United States Patent [19]

Guillou et al.

[11] Patent Number: Plant 7,271

[45] Date of Patent: Jul. 17, 1990

[54] VARIETY OF GERANIUM NAMED SIMONE

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 360,014

[22] Filed: Jun. 1, 1989

[30] Foreign Application Priority Data

Aug. 29, 1988 [FR] France ..... 7944

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenheim & Webb

[57] ABSTRACT

A new ivy geranium showing many favorable new traits that have been lacking in the ivy geraniums currently seen on the market. The variety has proven to be very heat tolerant both indoors and out. The vegetative growth is not as affected by high temperatures and the bloom burns less than is typical of this dark red color. The plant body is much stronger and fuller in habit, when compared to Yale, the current market ivy geranium in this color class. Cuttings are more readily available and root much faster than the current varieties. The deep, rich red color of the semi-double bloom appear velvet-like atop medium green foliage creating a full yet attractive hanging basket.

1 Drawing Sheet

BACKGROUND OF THE NEW PLANT

The present invention comprises a new and distinct cultivar of *Pelargonium×peltatum* known by the varietal name Simone (Oglevee Ltd. U.S. Plant Pat. No. 7,033, French No. 609 Guipolac). The new variety was discovered in a selective breeding program by Messrs. Jacques, Maurice and Bernard Guillou. The new variety is a selection from the crossing of Corsaire U.S. Plant Pat. No. 423×No. 85. The new variety has shorter foliage and earlier flowering than its parentage.

The new cultivar was discovered in 1985 at 55 rue Godard, 35400 Saint-Malo, France, was first asexually reproduced by cuttings during 1986 and 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., using full light, 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Feb. 17, 1988 and flowered on Sept. 15, 1988. Three 10 cm pots were potted into a 26 cm hanging basket and the plant was maintained until Feb. 24, 1989 when the color readings were taken. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium×peltatum.*

*Commercial.*—Ivy Geranium (U.S. Plant Pat. No. 7,033) Simone.

Form: Cascading mound habit.

Height: 17 cm above media surface.

Growth: Free branching, upright mound with cascading side growth, free and early flowering.

Strength: Has an upright mound shape while allowing outer branches to cascade over the sides of the pot.

Foliage: Stalked leaf attachment; very faint zone present.

Leaves:

*Size.*—5.5–7.5 cm across.

*Shape.*—Reniform, cordate base.

*Margin.*—Pedately lobed.

*Texture.*—Smooth; slightly reflective; leathery.

*Color.*—Top: Green Group 137A. Bottom: Yellow-Green Group 146A.

*Ribs and veins.*—Palmated venation; Color: Yellow-Green Group 146B.

Petioles: 2–5 cm in length;

*Color.*—Green Group 137C.

Stem:

*Color.*—Yellow-Green Group 146B.

*Internodes.*—2–5.5 cm in length.

THE BUD

Shape: Upright; hemispherical cluster.

Size: 1.5–2 cm across.

INFLORESCENCE

Blooming habit: Continuous; upright; semi-hemispherical; some shattering present.

Size: 7.5–8.5 cm across when fully open.

Borne: Florets on pedicel; pedicel on peduncle; umbel 4–6 cm above foliage canopy.

Florets:

*Form.*—Flat to slightly cupped.

*Color.*—Top: Red Group 45A with Red Group 53A shading in at the edges creating a velvet like color. Venation on upper three petals: Red-Purple Group 50A with a blotch of Red-Purple Group 61C between veins. Bottom: White with an overspray effect of Red Group 45B.

*Petals.*—10–12 in number, separate, not united; margin entire.

*Floret size.*—4.5–5 cm across.

*Texture and appearance.*—Smooth; from a distance the color appears a deep velvet red, only on close inspection do the individual colors stand out.

Petaloids:

*Quantity.*—4–6.

*Shape.*—Elongated, twisted, some with anther attached.

*Color.*—Red-Purple Group 61C.

Pedicel: 1–1.5 cm in length.

*Color.*—Yellow-Green Group 146B.

Peduncle: 7–12 cm in length.

*Color.*—Yellow-Green Group 146A. Arises from the node opposite leaf petiole.

Lasting quality: This variety is more heat tolerant and tends to be more shatter resistant than the current ivies.

REPRODUCTIVE ORGANS

Stamens:

*Anthers.*—2–3 cm in length.

*Filaments.*—9–10 cm in length; irregular shape; white to light pink in color.

*Pollen.*—Golden brown.

Pistils:

*Number.*—One; 6–7 part stigma.

*Length.*—8–10 mm.

*Stigma.*—6 or 7 parted; Red Purple.

*Style.*—3 mm in length; white.

Ovaries: Very pubescent; pale green; superior 3–5 mm in length, 2–3 mm across.

Fruit: None observed.

GENERAL CHARACTERISTICS

This distinct ivy geranium shows many favorable new traits that have been lacking in the ivy geraniums currently seen on the market.

This variety has proven to be very heat tolerant both indoors and out. The vegetative growth is not as affected by high temperatures and the bloom burns less than is typical of this dark red color.

The plant body is much stronger and full in habit as compared to Yale, the current market ivy geranium in this color class.

Cuttings are more readily available and root much faster than the current varieties.

The deep, rich red color of the semi-double bloom appear velvet-like atop medium green foliage creating a full yet attractive hanging basket.

Simone is best compared with Yale. Simone is more clear red, not as blue. Yale is a dark, almost blood-velvet. Simone has a hint of clearer red in the petal. Simone has superior foliage, darker foliage, with less Oedema problems, a physiological problem expressed in corky wounds all over the leaf underside. Simone is more heat tolerant and more uniform in habit, an earlier flowerer, and more floriferous.

We claim:

1. A new and distinct ivy geranium plant as shown and described herein, and characterized in heat tolerance both indoors and out, vegetative growth is not as affected by high temperatures and the bloom burns less than is typical of this dark red color, the plant body is strong and full in habit, the cuttings are more readily available and root much faster than the current varieties, and the deep, rich red color of the semi-double bloom appear velvet-like atop medium green foliage creating a full yet attractive hanging basket.

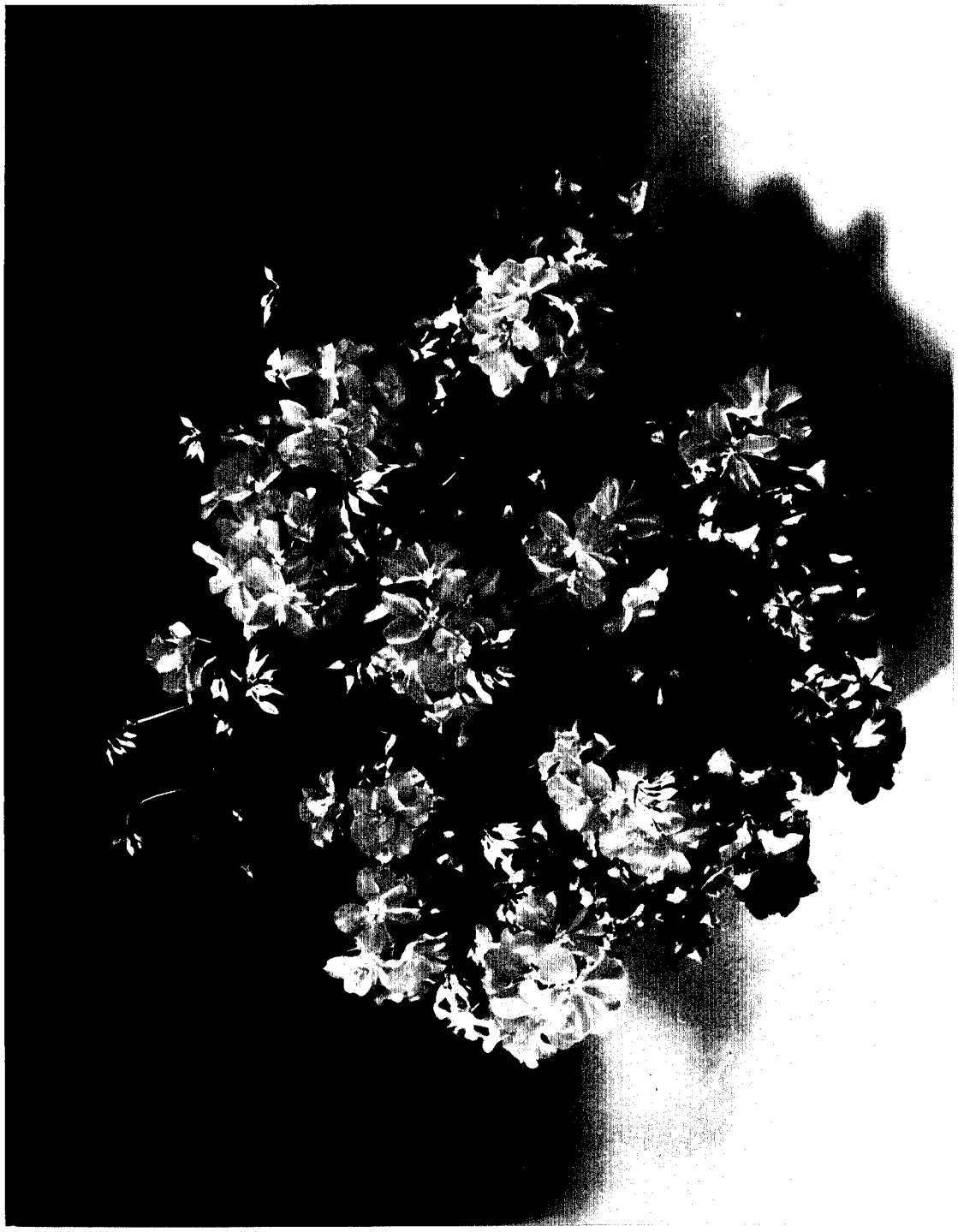

* * * * *